(12) United States Patent
Gordon

(10) Patent No.: US 6,964,686 B2
(45) Date of Patent: Nov. 15, 2005

(54) INTERVERTEBRAL DISC REPLACEMENT PROSTHESIS

(75) Inventor: Jeffrey D. Gordon, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 10/235,117

(22) Filed: Sep. 5, 2002

(65) Prior Publication Data
US 2005/0027363 A1 Feb. 3, 2005

Related U.S. Application Data (63) Continuation-in-part of application No. 09/572,057, filed on May 17, 2000, now Pat. No. 6,579,321.
(60) Provisional application No. 60/134,500, filed on May 17, 1999.

(51) Int. Cl.$^7$ .................................................. A61F 2/44
(52) U.S. Cl. .................................. 623/17.14; 623/17.16
(58) Field of Search ........................... 623/17.11, 17.16

(56) References Cited

U.S. PATENT DOCUMENTS

| | | | |
|---|---|---|---|
| 4,932,975 A | 6/1990 | Main et al. | |
| 5,320,644 A | 6/1994 | Baumgartner | |
| 5,415,704 A | * 5/1995 | Davidson | .................... 148/316 |
| 5,423,817 A | 6/1995 | Lin | |
| 5,507,816 A | 4/1996 | Bullivant | |
| 5,556,431 A | 9/1996 | Buttner-Janz | |
| 5,676,702 A | 10/1997 | Ratron | |
| 5,782,832 A | 7/1998 | Larsen et al. | |
| 5,827,328 A | 10/1998 | Buttermann | |
| 5,865,846 A | 2/1999 | Bryan et al. | |
| 5,888,223 A | 3/1999 | Bray, Jr. | |
| 5,888,226 A | 3/1999 | Rogozinski | |
| 5,895,428 A | 4/1999 | Berry | |
| 6,117,174 A | 9/2000 | Nolan | |
| 6,136,031 A | 10/2000 | Middleton | |
| 6,146,421 A | 11/2000 | Gordon et al. | |
| 6,296,664 B1 | * 10/2001 | Middleton | ............... 623/17.15 |
| 6,368,350 B1 | * 4/2002 | Erickson et al. | ......... 623/17.14 |
| 6,395,035 B2 | 5/2002 | Bresina et al. | |
| 6,579,321 B1 | 6/2003 | Gordon et al. | ........... 623/17.16 |
| 6,582,468 B1 | 6/2003 | Gauchet | ................... 623/17.16 |

FOREIGN PATENT DOCUMENTS

| | | | |
|---|---|---|---|
| EP | 538183 A1 | 4/1993 | |
| EP | 0 985 384 A1 | 3/2000 | ............. A61F/2/30 |
| FR | 2 734 148 A1 | 5/1995 | ............. A61F/2/04 |
| FR | 2799116 A1 * | 4/2001 | ............. A61F/2/44 |

OTHER PUBLICATIONS

Lee, Casey, et al.; *Development of a Prosthetic Intervertebral Disc*; Spine Surgery; Nov. 1, 1990; pp. S253–S255; vol. 16; No. 6.

(Continued)

*Primary Examiner*—Thomas Barrett
(74) *Attorney, Agent, or Firm*—Morris, Manning & Martin; Tim Tingkang Xia, Esq.

(57) ABSTRACT

An intervertebral disc prosthesis that comprises a deformable flexure with an axial cavity, the axial cavity extending along the axis of the flexure, and a slit defined in the perimeter surface of the flexure to provide flexibility to the disc member, the slit having a slit thickness. The slit may be in the form of a coil to impart a spring-like appearance and function. The intervertebral disc prosthesis further comprises a lower disc support housed in the axial cavity and an upper disc support housed in the axial cavity; with the lower and upper disc supports communicating with one another to provide support to the disc. The lower or upper disc support may alternatively be incorporated into the flexure.

5 Claims, 6 Drawing Sheets

OTHER PUBLICATIONS

Traynelis, Vincent, et al.; *Artificial Discs—The Future is Bright*; www.spineuniverse.com; Apr. 2001.

Article on PRODISC®; www.spinesolutionsinc.com.

Article on Intervertebral Dynamic Disc Spacer; www.link-spine.com; 2001.

"Biomechanics—BAK™ Interbody Fusion System" brochure; SulzerMedica, Sulzer Spine Tech; 1998.

"Patient Guide—BAK™ Interbody Fusion System" brochure; SulzerMedica, Sulzer Spine Tech; 1999.

Manufacturer Directory, ArtificialDisc.com, 2000.

Ray Threaded Fusion Cage™ informational brochure, Surgical Dynamics.

Enker, P., et al.; *Artificial Disc Placement, Preliminary Report With a 3–Year Minimum Follow–Up*; Spine, Mar. 9, 1993; pp. 1061–1070; vol. 18; No. 8.

Hedman, Thomas, et al.; *Design of an Intervertebral Disc Prosthesis*; Spine Surgery; Nov. 1, 1990; pp. S256–S259.

Kostuik, John P; *Intervertebral Disc Replacement, Experimental Study*; Clinical Orthopedics and Related Research, 1997; pp. 27–41; No. 337.

* cited by examiner

INTERVERTEBRAL DISC REPLACEMENT PROSTHESIS

This Application is a Continuation-In-Part of U.S. application Ser. No. 09/572,057, now U.S. Pat. No. 6,579,321 B1 filed May 17, 2000, the contents of which are incorporated herein by reference in its entirety. Ser. No. 09/572,057 claims priority to Provisional Application No. 60/134,500, filed May 17, 1999, now abandoned, the contents of which are incorporated herein by reference.

FIELD OF THE INVENTION

This invention relates, generally, to the field of intervertebral disc replacement prosthesis.

BACKGROUND OF THE INVENTION AND DESCRIPTION OF RELATED ART

Degenerative disc disease is a common condition of the intervertebral disc (IVD) of the spine characterized by disc height collapse with or without disc herniation, osteophyte formation, foramenal stenosis, facet hypertrophy, synovial cyst, and other symptoms. Any or a combination of these findings can lead to pain or neurological deficit. Many of the symptoms of degenerative disc disease may be alleviated by decompression of the neural structures and immobilization of the involved spinal segments. Immobilization is typically achieved in the long term by removal of the disc and placement of bone graft. Temporary immobilization to encourage incorporation of the bone graft can be achieved with placement of rigid hardware such as screws and rods.

While immobilization and a successful fusion may relieve the pain associated with nerve impingement, the long-term consequences of eliminating the motion of the IVD show a tendency toward increased risk of failure of the adjacent discs. The lack of motion at the fusion site places increased biomechanical demands on the adjacent discs causing them to degenerate prematurely.

Replacement prostheses have been suggested for degenerative disc disease to allow motion at the operative disc level. However these devices are devoid of stiffness and stability and rely on the remaining spinal elements, such as the ligaments, muscles and remaining IVD tissue, namely the annulus fibrosis, for stability. For example, U.S. Pat. No. 5,556,431 to Buttner-Janz, U.S. Pat. No. 5,507,846 to Bullivant and U.S. Pat. No. 5,888,226 to Chaim, all of which are incorporated herein by reference, describe prostheses that comprise ball and socket type joints. These inventions rely on stretching the annulus fibrosis to put the prosthesis into compression to gain stiffness. But there is risk of altering the spine's biomechanics by increasing the disc height past the normal range and risk of damage to the annulus fibrosis. If the disc space is not stretched enough an unstable spinal segment could result, possibly leading to pain and further injury. Furthermore, all of these prior art disc replacement prostheses consist of several parts that are not connected. Implantation entails insertion of several separate pieces that must be properly aligned during surgery. The surgery is often performed with a minimal incision offering limited access to the insertion site. Perfect alignment after insertion could be difficult.

Other prostheses have been suggested (for example, see U.S. Pat. No. 6,136,031 to Middleton, U.S. Pat. No. 5,320,644 to Baumgartner, U.S. Pat. No. 5,827,328 to Buttermann and U.S. Pat. No. 5,676,702 to Ratron, all of which are incorporated herein by reference) which have their own inherent stiffness, but do not take into account that axial loads placed on the spine during activity are generally much larger than bending loads. Therefore, these prostheses would either bottom out under axial loads and offer no response to bending loads, or be stiff enough to support the axial loads and thereby too stiff to flex under bending loads.

What is needed is an intervertebral disc prosthesis that assists in alleviating the symptoms of degenerative disc disease without sacrificing normal spinal mechanics.

SUMMARY OF THE INVENTION

An object of the present invention is to provide an intervertebral disc prosthesis that assists in alleviating the symptoms of degenerative disc disease without sacrificing normal spinal biomechanics, and therefore not compromising the health of adjacent discs.

Another object of the present invention is to provide an intervertebral disc prosthesis that performs effectively and efficiently within a patient's spine over a long period of time.

Furthermore, another object of the present invention is a prosthesis that is easily implanted and mimics both the motion and the stiffness of a normal disc.

Embodiments of this invention include a prosthesis that is comprised of a flexible element enclosing supports, or bearing surfaces that resemble a ball-and-socket joint. In all embodiments, alignment of the bearing surfaces may be achieved during manufacture, not during surgery. Therefore, implantation involves placement of a single unit. The implant has the ability to mimic the motion of a normal healthy disc and also to approximate the stiffness of the disc material that it is replacing. These embodiments may be sized to accommodate a range of disc space geometries for the cervical, thoracic or lumbar spine.

A preferred embodiment of the present invention is an implantable intervertebral disc replacement prosthesis that comprises a deformable flexure with an axial cavity, the axial cavity extending along the axis of the flexure and a slit defined in the perimeter surface of the flexure to provide flexibility to the disc member, the slit having a slit thickness. This embodiment further comprises a lower disc support housed in the axial cavity and an upper disc support housed in the axial cavity; with the lower and upper disc supports communicating with one another to provide support to the disc.

Alternatively, either the upper or lower disc support means may be incorporated into the flexure in the form of a concave axial cavity or a convex protuberance.

These and other embodiments will be apparent from the disclosure and claims.

DETAILED DESCRIPTION OF THE PREFERRED EMBODIMENTS

Figure 1:
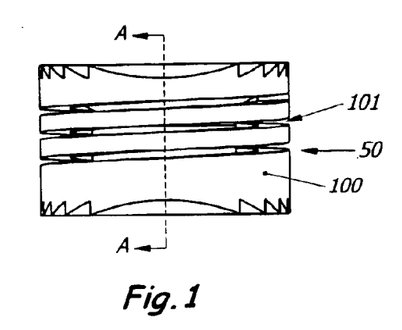
FIG. 1 is a posterior view of a preferred embodiment of the present invention.
Figure 2:
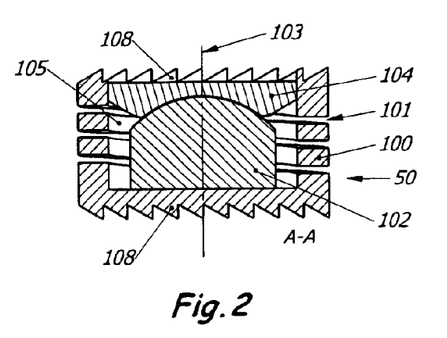
FIG. 2 is a lateral, cross-sectional view of a preferred embodiment taken along line A—A of FIG. 1.
Figure 3:
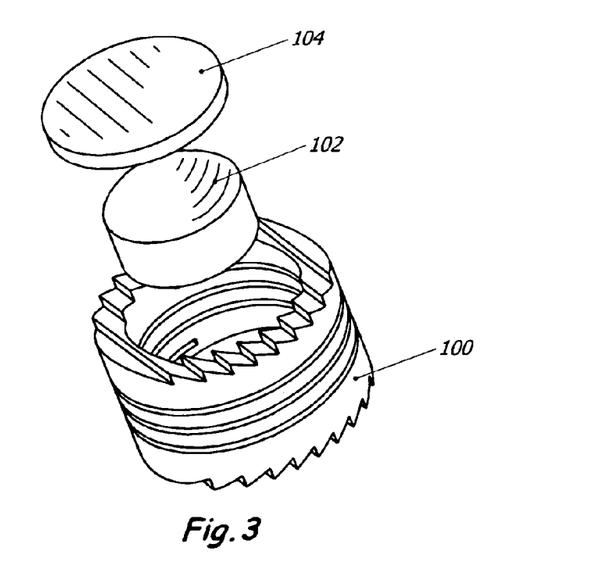
FIG. 3 is an exploded view of the preferred embodiment depicted in FIGS. 1 & 2.

A preferred embodiment of the invention is shown in FIGS. 1, 2 & 3. The disc replacement prosthesis of the present invention is an implantable intervertebral disc replacement prosthesis 50 containing a flexure 100 which has an axis 103. The flexure 100 is formed from a solid piece of material in which a blind hole is bored defining an axial cavity 105 which extends along the axis 103. In this embodiment, a helical slit 101 is cut in the perimeter surface, with the axis of the helix approximately coincident with axis 103 of disc member 50, so that the perimeter surface resembles a helical coil or spring.

The disc replacement of the present embodiment further comprises a lower disc support 102 housed in the axial cavity 105, and an upper disc support 104 housed in the axial cavity 105, with the lower and upper disc supports communicating with one another to provide support to the disc. The lower and upper disc supports also act as bearing elements, and may communicate in a ball-and-socket type arrangement. These elements (i.e. the lower and upper disc supports) communicate to act as a transferor of axial compression loads. Lower disc support 102 may or may not be rigidly attached to flexure 100. Upper disc support 104 may be rigidly attached to the flexure 100 by press-fit, retaining ring, pins, welds or some other means, and also forms the upper surface of the disc member.

All embodiments of the present invention are to be made from a surgically implantable biocompatible material. The preferred material for the flexure 100 should possess high fatigue strength such as titanium, titanium alloy, or stainless steel. The material for the upper and lower disc supports 104 and 102 should possess excellent wear resistance and compressive strength. Ceramics, titanium, titanium alloy, stainless steel, cobalt chrome, composites, or polymers should preferably be used for these elements. Alternatively, a biocompatible material with a wear reducing coating could be used. For example, a titanium nitride coating may be used on the supports or the flexure.

Attachment of the disc member 50 to the adjacent vertebrae should involve both immediate and long-term fixation. Immediate fixation can be achieved with a mechanical bone attachment means. For example, the upper and/or lower surfaces may include mechanical elements such as teeth 108. Also, The entire superior and inferior surfaces, including teeth 108 can be coated with a bone ingrowth inducing osteoconductive substance such as sintered beads or sintered wires or an osteoinductive coating such as hydroxyapatite for long-term fixation. Osteoinductive and osteoconductive coatings have been used extensively in joint replacement for many years and have been proven to be effective.

The flexure 100 allows the disc member 50 to react to bending loads by flexing. The geometry of helical slit 101 can determine the stiffness of flexure 100 and therefore the stiffness of disc member 50. For example, to produce a more flexible implant the thickness of helical slit 101 can be increased so that less material of flexure 100 remains. Also the number of coils will determine the stiffness of the flexure. The spring action of flexure 100 will allow rotation and will have an inherent torsional stiffness that is also determined by the geometry of helical slit 101. The range of motion of disc member 50 is determined by the point at which flexure 100 bottoms out (the point at which a bending load causes adjacent coils to come into contact). The range of motion is determined by the space between the coils, which is equivalent to the thickness of helical slit 101 multiplied by the number of coils. Therefore helical slit 101 can be tailored to match the mechanical and kinematical characteristics of a normal disc at any level in the spine.

Figure 4:
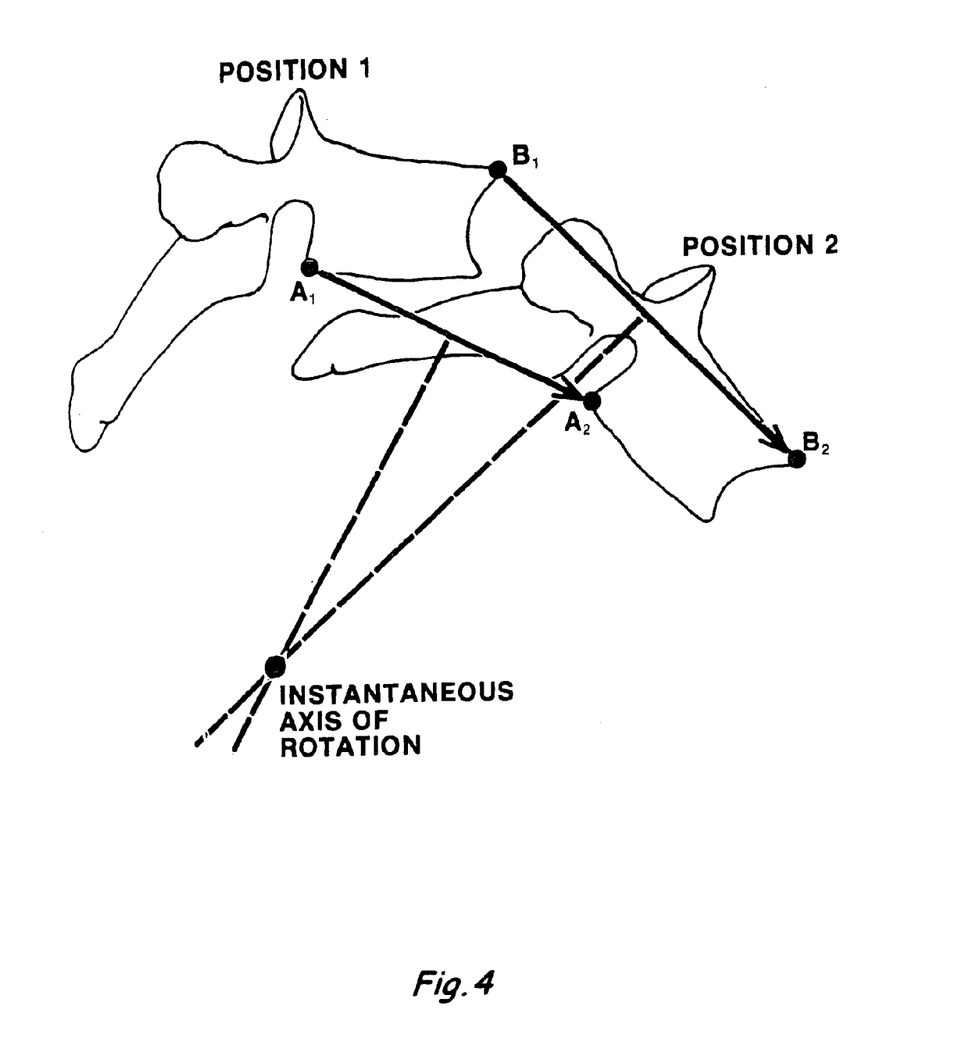
FIG. 4 is a diagram demonstrating the method of finding the instantaneous axis of rotation of a vertebra in motion relative to a fixed point.

The instantaneous axis of rotation (IAR) is a parameter that characterizes how one body rotates with respect to another body (or a fixed point) in planar motion. Normal spinal motion can be characterized as planar (2D) for pure flexion-extension. FIG. 4 demonstrates the general method of determining the IAR of the motion of a body from two positions. Translation vectors $A_1$, $A_2$ and $B_1$, $B_2$ are drawn from points before the motion to corresponding points after the motion. The intersection of the perpendicular bisectors of these translation vectors is the IAR of the motion.

The preferred embodiment of the present invention incorporates a mobile IAR. The ball-and-socket arrangement of the preferred embodiment of FIGS. 1, 2, & 3 may comprise a lower disc support 102 having a convex surface, and an upper disc support 104 having a surface suitable for receiving and communicating with the convex surface of lower disc support 102. The convex surface of lower disc support 102 may vary. For instance, it may range from a partial hemisphere to a full hemisphere or it may be an elongated element with a rounded or partially rounded end. Motion at the interface between lower disc support 102 (as seen in FIG. 2) and upper disc support 104 has an IAR at the center of the radius of the bearing surface of lower disc support 102. However, this embodiment also allows translation between lower disc support 102 and flexure 100. The combination of rotation and translation allows a range of possible IAR's.

Figure 5:
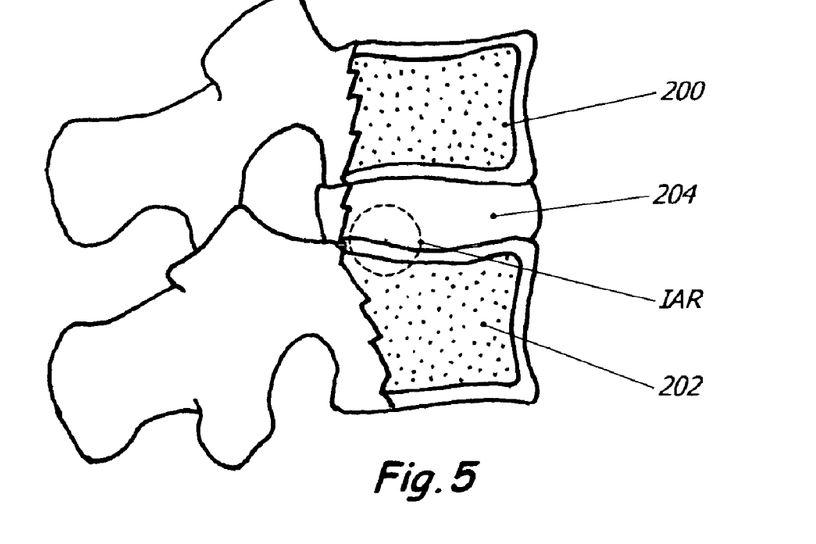
FIG. 5 is a lateral cross-sectional view of a normal spinal motion segment.
Figure 6:
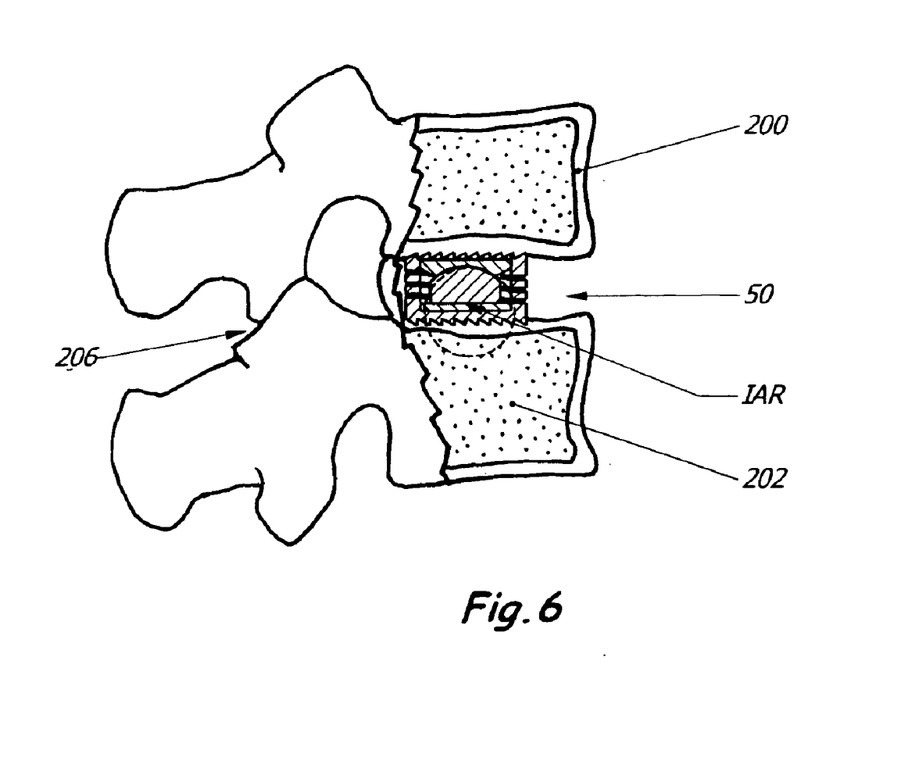
FIG. 6 is a lateral cross-sectional view of a spinal motion segment showing placement of an embodiment of the invention in the disc space.

FIG. 5 is a cross-sectional view of a motion segment including a superior vertebra 200, IVD 204 and an inferior vertebra 202. The IAR for adjacent vertebrae in the normal lumbar spine has been shown to be located on or near the superior endplate of the inferior vertebra 202 of a motion segment, as shown. FIG. 6 shows the same cross-section of the spine as FIG. 5, but with placement of disc member 50. In order to prevent unnatural loading of the facet joints 206, the correct IAR must be maintained. The mobile IAR described above may allow correct IAR of motion between superior vertebra 200 and inferior vertebra 202 after implantation of disc element 50.

Figure 7:
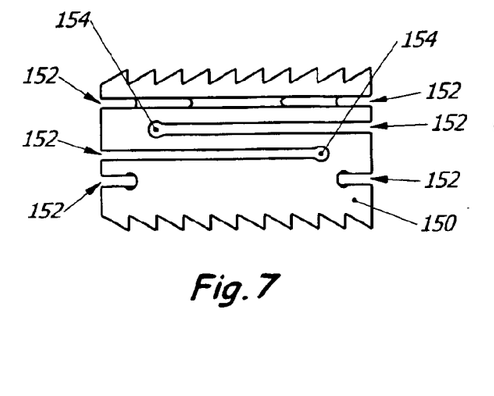
FIG. 7 is a lateral view of an alternative embodiment of the present invention with slits or cuts that terminate in perimeter openings
Figure 8:
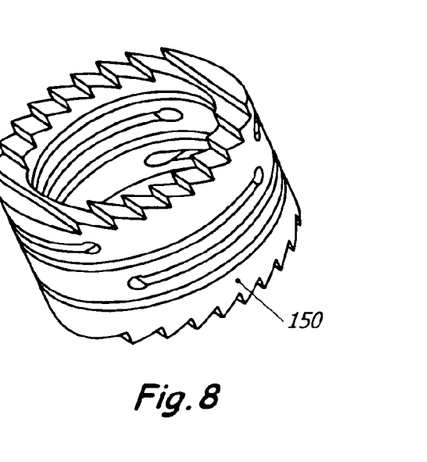
FIG. 8 is an isometric view of the alternative embodiment shown in FIG. 7.

FIGS. 7 and 8 show an alternative embodiment where approximately horizontal perimeter slits 152 have been cut into flexure 150 instead of a helical-type slit. Preferably, the slit is substantially at a right angle to the axis of the disc member. The orientation of the slits is such that at least one slit is opened and at least one slit is closed under the action of bending loads imposed at any plane through the axis of the disc member. In the embodiment depicted in the drawings, each slit terminates in a hole or a perimeter opening 154, with a diameter that is larger than the thickness of the slit to reduce stress concentration. Preferably, the perimeter opening is circular-shaped. The depth, thickness and number of the perimeter slits 152 as well as the size of perimeter opening 154 determine the stiffness of the disc member. The thickness and number of perimeter slits 152 determine the range of motion of the prosthesis.

Figure 9:
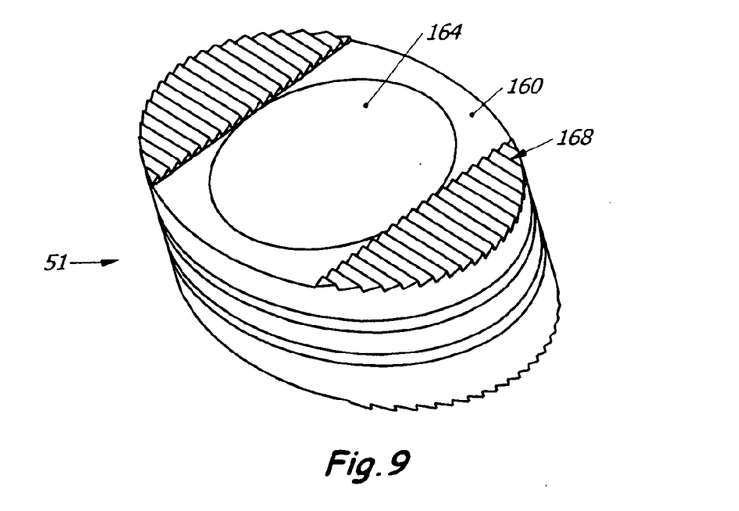
FIG. 9 is an isometric view of an alternative embodiment of the present invention with an oval shape

Disc 50 can be made into a variety of shapes, as long as the spirit of the invention is not adversely affected. That is, the disc prosthesis of the present invention may have a surface (such as, for example, the upper surface or the lower surface) that is flat, convex in shape or is otherwise shaped to fit the cavity of a vertebral endplate. Furthermore, from a top (superior-to-inferior) view, disc member 50 may be of a variety of shapes: for example circular, kidney-shaped, or oval-shaped. FIG. 9 shows an alternative embodiment of a disc 51 of the invention in which flexure 160 is oval shaped. Teeth 168 and upper disc support 164 are similar to those described above.

Figure 10:
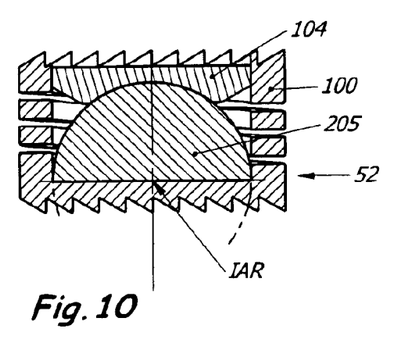
FIG. 10 is a cross-sectional view of an alternative embodiment of the present invention with a fixed axis.
Figure 11:
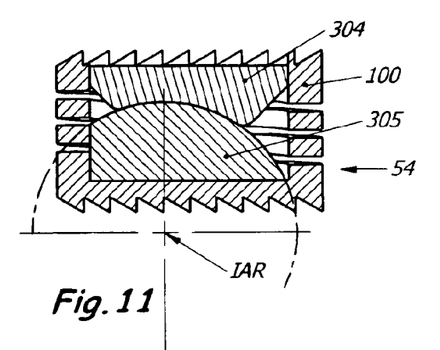
FIG. 11 is a cross-sectional view of an alternative embodiment of the present invention with a shifted axis.

Multiple alternative embodiments are also shown. A cross sectional view of an alternative embodiment of a disc 52 of the invention is shown in FIG. 10 that has a fixed IAR at the center of the radius of hemispherical lower disc support 205. The flexure 100 and the upper disc support 104 are also shown. FIG. 11 shows a cross sectional view of an alternative embodiment of a disc 54 of the invention in which the IAR has been shifted down and left, demonstrating that the IAR can be tailored to match the IAR of a healthy disc simply by altering the radius of curvature and the center of the radius of curvature of partial hemispherical lower disc support 305. Upper disc support 304 has been made to communicate with partial hemispherical disc support 305. The flexure 100 is also shown.

Figure 12:
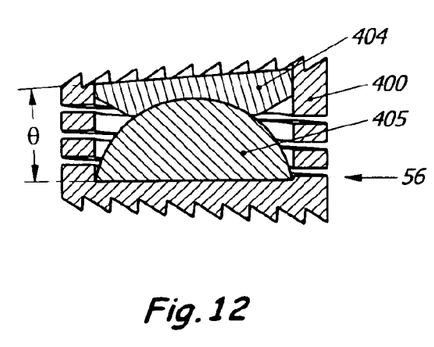
FIG. 12 is a cross-sectional view of an alternative embodiment of the present invention with an angulated flexure.

FIG. 12 shows angulated disc member 56 with angulated flexure 400 and augmented lower disc support 405 and augmented upper disc support 404. The angle θ incorporated into angulated disc member 56 is meant to maintain the natural lordosis of the lumbar or cervical spine or the natural kyphosis of the thoracic spine. This angle could be matched to any lordosis or kyphosis of a disc level being replaced.

Figure 13:
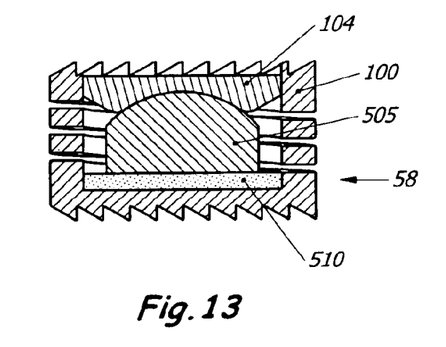
FIG. 13 is a cross-sectional view of an alternative embodiment of the present invention with a lower seat.

FIG. 13 shows a disc 58 of the present invention with the addition of a lower seat member 510 communicated with the axial cavity of flexure 100. In the case that a metal material is used for flexure 100 and a harder ceramic material is used for shortened lower disc support 505, lower seat member 510 could also be made of ceramic so that all elements experiencing sliding contact would gain the advantage of low wear ceramic on ceramic contact. The upper disc support 104 is also shown.

Figure 14:
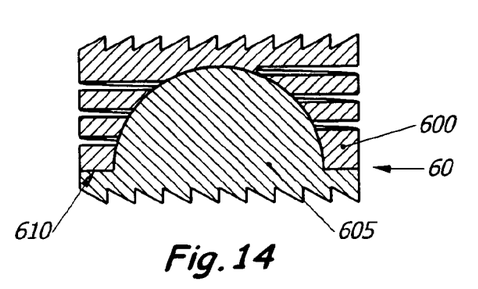
FIG. 14 is a cross-sectional view of an alternative embodiment of the present invention where the flexure incorporates an upper disc support means.

Another alternative embodiment of the disc 60 of the present invention is pictured in FIG. 14. A concave recess is created in flexure 600 which is meant to communicate with a flanged lower disc support 605. In this way, the upper disc support is incorporated into flexure 600. Flexure 600 may be rigidly attached to flange 610 of flanged lower disc support 605 by weld, pins, retaining ring or some other means.

Figure 15:
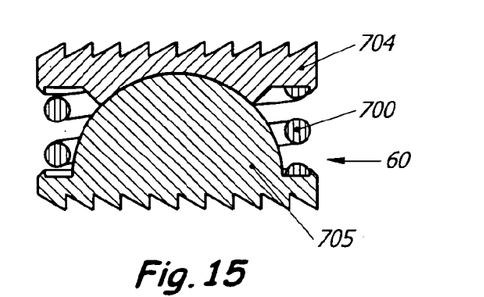
FIG. 15 is a cross-sectional view of an alternative embodiment of the present invention with a wire spring.

Another alternative embodiment of the disc 60 is pictured in FIG. 15. A spring element 700 is a conventional helical spring made by forming a wire into a helix. Flanged upper disc support 704 and flanged lower disc support 705 are made to communicate with each other and to communicate with spring 700. Spring 700 may be rigidly attached to either or both flanged upper disc support 704 or flanged lower disc support 705.

Figure 16:
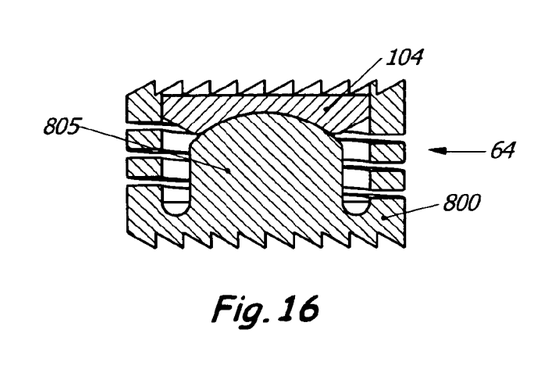
FIG. 16 is a cross-sectional view of an alternative embodiment of the present invention where the flexure incorporates a lower disc support means.

Another alternative embodiment if the disc 64 of the present invention is pictured in FIG. 16. Flexure 800 incorporates a protuberance 805 which serves as a lower disc support. Upper disc support 104 is made to communicate with protuberance 805. Therefore, the lower disc support is incorporated into flexure 800.

The disc prosthesis of the present invention may be inserted into the spine using standard medical procedures. For example, see Benzel, Spine Surgery: Techniques, Complication Avoidance, and Management, 1999, the contents of which are incorporated herein by reference. Particularly see Benzel, at Section 11, pages 142–192. Additionally, when inserting the disc prostheses of the present invention, the prosthesis may be inserted so that the lower disc support is superior to (from a top view) to the upper disc support. In other words, the disc prosthesis of the present invention mat be used such that, when looking at the spine, the upper disc support as described herein is on the bottom and the lower disc support is on top.

All cited patents and publications referred to in this application are herein expressly incorporated herein by reference.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of the following claims.

I claim:

1. An implantable intervertebral disc replacement prosthesis, comprising:

an upper surface and a lower surface;

a deformable flexure with a perimeter surface and an axial cavity, the axial cavity extending along the axis of the flexure;

a slit defined in the perimeter surface of the flexure to provide flexibility to the flexure, the slit having a slit thickness;

a lower disc support housed in the axial cavity; and an upper disc support housed in the axial cavity, wherein the lower disc support and the upper disc support communicate with one another in a ball-and-socket-type arrangement.

2. The implantable intervertebral disc replacement prosthesis of claim 1, wherein the lower disc support has a convex surface, and the upper disc support has a surface suitable for receiving and communicating with the convex surface of the lower disc support.

3. The implantable intervertebral disc replacement prosthesis of claim 1, wherein the upper disc support and the lower disc support have a coating that comprises a titanium nitride material, respectively.

4. An implantable intervertebral disc replacement prosthesis, comprising:

an upper surface and a lower surface;

a deformable flexure with a perimeter surface that defines an axial cavity, the axial cavity extending along the axis of the flexure;

a slit defined in the perimeter surface of the flexure to provide flexibility to the flexure, the slit having a slit thickness; and a lower disc support housed in the axial cavity, wherein the lower disc support is received by the axial cavity of the flexure, and the lower disc support and the axial cavity of the flexure communicate in a ball-and-socket-type arrangement.

5. The implantable intervertebral disc replacement prosthesis of claim 4, wherein the lower disc support has a convex surface, and the axial cavity of the flexure has a surface suitable for receiving and communicating with the convex surface of the lower disc support.

* * * * *